United States Patent [19]

Miyazaki et al.

[11] 3,932,475

[45] Jan. 13, 1976

[54] PROCESS FOR PRODUCING TRIMETHYL-P-BENZOQUINONE

[75] Inventors: Tetuo Miyazaki, Nara; Sunao Munemiya, Amagasaki; Akira Tasaka, Takatsuki, all of Japan

[73] Assignee: Sumitomo Chemical Company, Limited, Osaka, Japan

[22] Filed: June 27, 1973

[21] Appl. No.: 374,165

[30] Foreign Application Priority Data

| June 27, 1972 | Japan | 47-64715 |
| July 12, 1972 | Japan | 47-70262 |
| July 12, 1972 | Japan | 47-70263 |
| Sept. 7, 1972 | Japan | 47-90224 |

[52] U.S. Cl. .......................... 260/396 R; 260/623 H
[51] Int. Cl.² .................................. C07C 49/64
[58] Field of Search ........................... 260/396 R

[56] References Cited

UNITED STATES PATENTS

| 3,549,669 | 12/1970 | Clemens, Jr. | 260/396 R |
| 3,549,670 | 12/1970 | Spousta | 260/396 R |
| 3,796,732 | 3/1974 | Brenner | 260/396 R |

*Primary Examiner*—Vivian Garner
*Attorney, Agent, or Firm*—Sughrue, Rothwell, Mion, Zinn & Macpeak

[57] ABSTRACT

A process for producing trimethyl-p-benzoquinone by halogenating 2,3,5- or 2,3,6-trimethylphenol and oxidizing the resulting 2,3,5- or 2,3,6-trimethyl-4-halogenophenol, is disclosed. The resulting compound can readily be converted to trimethylhydroquinone useful as a starting material for producing vitamin E.

10 Claims, No Drawings

PROCESS FOR PRODUCING TRIMETHYL-P-BENZOQUINONE

BACKGROUND OF THE INVENTION

1. Field of the Invention

The present invention relates to a process for synthesizing trimethyl-p-benzoquinone from trimethylphenol and, more particularly, it relates to a process for producing trimethyl-p-benzoquinone in high yield by introducing a halogen group to p-position of 2,3,5- or 2,3,6-trimethylphenol and oxidizing the resulting 2,3,5- or 2,3,6-trimethyl-4-halogenophenol.

2. Description of the Prior Art

As has already been well known, trimethyl-p-benzoquinone is readily reduced to trimethylhydroquinone, which is important as a starting material for synthesizing vitamin E.

There have heretofore been various literatures and patents as to the process for producing trimethyl-p-benzoquinone by oxidizing trimethylphenol. For example, there is a description in "Journal of Organic Chemistry", 4, 318(1939), that trimethyl-p-benzoquinone is obtained in 50 percent yield by oxidizing trimethylphenol with chromic acid in an aqueous sulfuric acid solution. Furthermore, in this literature, trimethylphenol is diazotized with a diazotizing solution and hydrogenated to produce trimethyl-p-aminophenol, which is then oxidized with ferric chloride to obtain trimethyl-p-benzoquinone in 95 percent yield. However, the above-described processes are economically disadvantageous since many steps are involved and expensive chemicals are used.

Also, in the process described in Japanese Pat. Publication No. 38063/70 (German Pat. OLS No. 1,814,652), 2,3,6-trimethylphenol is dissolved in acetic acid and oxidized with a dilute nitric acid using sodium nitrite as a catalyst to obtain trimethyl-p-benzoquinone in maximum yield of 69.6 percent. This process is simple and is considered to be a good one. However, the yield is a little low.

Various oxidizing processes are under examination also in other literatures. However, there are produced in many cases a diphenoquinone-homolog product and the selectivity to the desired trimethyl-p-benzoquinone is low.

SUMMARY OF THE INVENTION

As a result of intensive investigations on the process for synthesizing trimethyl-p-benzoquinone inexpensively with high yield, the inventors have achieved the present invention. That is, although major portion of trimethylphenol is converted to a diphenoquinone-homolog compound by a usual direct oxidation, the inventors have examined substituents which prevent the formation of the diphenoquinone-homolog compound and yet does not prevent the oxidation and, as a result, have discovered to substitute the p-position with a halogen group. Preferably enough, the oxidation of trimethyl-p-halogenated-phenol proceeds without an induction period, i.e., the oxidation reaction starts immediately after adding an oxidizing agent such as nitric acid to produce a desired trimethyl-p-benzoquinone in the absence of catalyst with almost no side reactions. Further preferably enough, halogen substituent has an ortho-para orientation property with respect to the hydroxy group of the starting phenol and is introduced almost to p-position at a low temperature. In particular, when 2,3,6-trimethylphenol is used as a starting material, the p-position is quantitatively substituted by halogen since the ortho position is substituted by a methyl group. The halogenated trimethylphenol may be oxidized without recovering the halogenated product from the reaction solution. Of course, when the halogenated trimethylphenol was oxidized after removing the solvent, taking out the product and dispersing in water or dissolving a suitable solvent, the reaction similarly occurred immediately with no change in yield.

DETAILED DESCRIPTION OF THE INVENTION

In the halogenation reaction which is the first reaction in the present invention, there are used as a reaction solvent those which can be used in the usual chlorination reaction, such as acetic acid, carbon tetrachloride, carbon disulfide, etc. However, any solvent may be used so long as it does not itself participate in the halogenation reaction and can dissolve the starting trimethylphenol. But, considering the subsequent oxidation procedure, carbon tetrachloride is the best from the viewpoint of easiness in recovery of the solvent and in reaction procedures.

As the substituent halogen, any of chlorine, bromine and iodine may be used. However, chlorine is economically advantageous since it is inexpensive.

The reaction may be conducted at 0°C – 100°C, preferably 20°C – 80°C.

Usually, the reaction proceeds almost quantitatively in the absence of catalyst. However, in order to improve the selectivity of introducing halogen particularly to p-position, iron powder, sodium acetate, or a catalyst using for Friedel-Crafts reaction such as aluminum chloride, iron chloride, etc., and the like may be used. In particular, a small amount of iodine upon chlorination or bromination is effective.

In the oxidation reaction of the halogenated trimethylphenol, there may be used as an oxidizing agent those which are commonly known, such as chromic acid, nitric acid, potassium permanganate, peroxide, and the like. Of these oxidizing agents, nitric acid provides the best results and is the most inexpensive. Any of concentrated nitric acid, dilute nitric acid and fuming nitric acid provides the same results.

As the solvent for the oxidation, there may be used water, acetic acid, aliphatic hydrocarbon (e.g., hexane, heptane, etc.), halogen-substituted aliphatic hydrocarbon (e.g., chloroform, dichloromethane, methyl chloride, carbon tetrachloride, etc.). Of these solvents, water, acetic acid and carbon tetrachloride are preferable. Furthermore, where the oxidation reaction subsequent to the halogenation reaction is conducted without separating the intermediate, carbon tetrachloride is particularly preferable from the viewpoint of easiness in reaction procedures and in recovery of the solvent.

The present invention will now be described in greater detail by Examples and Comparative Examples, which, however, should not be construed to be limitative but illustrative only.

EXAMPLE 1

A. 136 g (1 mole) of 2,3,6-trimethylphenol was dissolved in 1000 g of acetic acid, and 75 g (1.06 moles) of chlorine gas was bubbled thereinto at a room temperature in one hour.

After the completion of bubbling, nitrogen gas was bubbled thereinto to remove hydrogen chloride gas, followed by distilling off acetic acid to obtain 169.8 g of the residue. The residue had a melting point of 79.5°–80.5°C. The thus obtained product was confirmed to be 2,3,6-trimethyl-4-chlorophenol by elementary analysis, infrared spectrum and NMR spectrum.

B. 17.0 g (0.1 mole) of 2,3,6-trimethyl-4-chlorophenol obtained in the above (A) was dispersed in 40 g of water, and 10 g of concentrated nitric acid was added dropwise thereto in 30 minutes under vigorous stirring. The reaction immediately took place and a yellowish brown oil dispersed in water produced. After continuing the stirring for another 30 minutes, the reaction solution was subjected to steam distillation. At the time when the yellow color of the distillate disappeared, steam distillation was discontinued and the distillate was extracted with ether. The ether layer was washed with an aqueous sodium bicarbonate solution and, after drying over sodium sulfate (anhydrous) ether was distilled off to obtain 13.6 g of 2,3,6-trimethyl-p-benzoquinone (90.6 percent in yield).

EXAMPLE 2

In manner analogous to Example 1, but employing 17.0 g (0.1 mole) of 2,3,5-trimethyl-4-chlorophenol obtained in the same manner as in Example 1 (A) in place of 2,3,6-trimethyl-4-chlorophenol used in Example 1 (B), there was obtained 13.2 g of 2,3,5-trimethyl-p-benzoquinone (88% in yield).

EXAMPLE 3

Oxidation reaction was conducted using 17.0 g (0.1 mole) of 2,3,6-trimethyl-4-chlorophenol obtained in Example 1 (A) changing the amount of the solution containing 10 g of nitric acid. Results are shown in Table 1.

Table 1

| Water (g) | 0 | 10 | 20 | 60 |
|---|---|---|---|---|
| Yield (%) | 90 | 88 | 92 | 92 |

It can be seen from Table 1 that difference in concentration of nitric acid caused no difference in yield.

EXAMPLE 4

17.0 g (0.1 mole) of 2,3,6-trimethyl-4-chlorophenol obtained in Example 1 (A) was oxidized with a solution prepared by dissolving 15 g of chromic acid in 20 g of acetic acid. The reaction solution was treated in the same manner as in Example 1 to obtain 12.6 g of 2,3,6-trimethyl-p-benzoquinone (84% in yield).

EXAMPLE 5

17.0 g (0.1 mole) of 2,3,6-trimethyl-4-chlorophenol obtained in Example 1 (A) was dissolved in 100 g of acetic acid, and 10 g of concentrated nitric acid was added dropwise thereto in 30 minutes under stirring. The reaction proceeded immediately. After stirring for another 30 minutes, the reaction solution was subjected to steam distillation. The same treatment as in Example 1 was conducted to obtain 13.8 g of 2,3,6-trimethyl-p-benzoquinone (92.0 percent in yield).

EXAMPLE 6

17.0 g (0.1 mole) of 2,3,6-trimethyl-4-chlorophenol obtained in Example 1 (A) was dissolved in 50 g of carbon tetrachloride, and a mixture of 10 g of commercially available concentrated nitric acid (64% by weight) and 20 g of water was added dropwise thereto in 30 minutes under vigorous stirring at 40°C. After the completion of the dropwise addition, stirring was continued for another 30 minutes. Thereafter, the carbon tetrachloride layer was separated out followed by removing carbon tetrachloride. It was confirmed by gas chromatography analysis that 15.5 g of the resulting residue contained 14.3 g of trimethylbenzoquinone. (Yield: 95.3 percent) The remaining residue was rectified under reduced pressure (at 3 mmHg) to obtain 14.0 g of 85° – 90°C distillate. This was nearly pure 2,3,6-trimethyl-p-benzoquinone.

EXAMPLE 7

A. 136 g (1 mole) of 2,3,6-trimethylphenol was dissolved in 900 g of acetic acid, and a solution prepared by dissolving 160 g (1 mole) of bromine in 100 g of acetic acid was added dropwise thereto in one hour. The reaction was conducted at a room temperature. Upon dropwise addition, the color of bromine instantly disappeared and the reaction proceeded immediately.

After the completion of the dropwise addition, hydrogen bromide formed was expelled with nitrogen gas to obtain quantitatively 2,3,6-trimethyl-4-bromophenol having a melting point of 91° – 92°C. The chemical structure was confirmed in the same manner as in Example 1 (A).

B. 21.5 g (0.1 mole) of 2,3,6-trimethyl-4-bromophenol obtained in the above (A) was dissolved in 100 g of acetic acid, and 10 g of concentrated nitric acid was added dropwise thereto in 30 minutes under stirring. The reaction proceeded immediately. After continuing the stirring for another 30 minutes, the reaction solution was subjected to steam distillation. The same treatment as in Example 1 (B) was conducted to obtain 12.0 g of 2,3,6-trimethyl-p-benzoquinone. (Yield: 80.0 percent)

EXAMPLE 8

13.6 g (0.1 mole) of 2,3,6-trimethylphenol was dissolved in 100 g of acetic acid, and 7.4 g (0.104 mole) of chlorine gas bubbled thereinto at 20° – 30°C under stirring. Gas chromatography at this stage showed that p-chloro derivative was produced fairly quantitatively. 10 g of commercially available concentrated nitric acid (63 percent) was added dropwise thereto in 30 minutes without removing acetic acid. The temperature rose to 30°C. After dropwise addition, the stirring was continued for another 30 minutes, and then the reaction solution was subjected to steam distillation. The steam distillation was discontinued at the time when the yellow color of the distillate disappeared, and the distillate was extracted with ether. The ether layer was washed with an aqueous solution of sodium bicarbonate and dried over sodium sulfate (anhydrous), followed by distillating off ether. Thus, there was obtained 13.5 g (90 percent in yield) of 2,3,6-trimethyl-p-benzoquinone.

EXAMPLE 9

2,3,5-trimethylphenol was reacted in the same manner as in Example 8 to obtain 13.2 g of 2,3,5-trimethyl-p-benzoquinone. (Yield: 88 percent)

EXAMPLE 10

Halogenation and subsequent oxidation were conducted in the same manner as in Example 8 except for adding 0.068 g of iodine to the acetic acid solution of 2,3,6-trimethylphenol upon chlorination. Thus, there was obtained 14.2 g (94.7 percent in yield) of 2,3,6-trimethyl-p-benzoquinone.

EXAMPLE 11

Chlorination was conducted in the same manner as in Example 8, and the chlorinated product was oxidized with a solution prepared by dissolving 15 g of chromic acid in 20 g of acetic acid. The same treatment as in Example 1 was conducted to obtain 12.6 g (84 percent in yield) of 2,3,6-trimethyl-p-benzoquinone.

EXAMPLE 12

1000 g of carbon tetrachloride was charged in a 5-liter four neck flask equipped with a stirrer, a condenser, a chlorine-bubbling pipe and a thermometer, and 408 g (3 moles) of 2,3,6-trimethylphenol was dissolved therein. Thereafter, 210 g (3 moles) of chlorine gas was bubbled thereinto at 40°C in 2 hours. After the completion of the bubbling, a mixture of 210 g of a commercially available nitric acid (63 percent by weight) and 600 g of water was immediately added dropwise thereto at 40°C for 2 hours. After the completion of the dropwise addition, the stirring was continued for further 1 hour. Then, the reaction solution was allowed to stand, and the separated lower layer of carbon tetrachloride was taken out, and washed with water, followed by distilling off carbon tetrachloride. Thus, 460 g of the residue was obtained as a red oil, in which 405 g of 2,3,6-trimethyl-p-benzoquinone was included. (90 percent in yield).

EXAMPLE 13

In manner analogous to Example 3, but employing 2,3,5-trimethylphenol in place of 2,3,6-trimethylphenol, there was obtained 2,3,5-trimethyl-p-benzoquinone in 85 percent yield.

EXAMPLE 14

In manner analogous to Example 12, but adding 2 g of iodine to the carbon tetrachloride solution of 2,3,6-trimethylphenol, there was obtained 475 g of distillation residue, in which 428 g (95 percent in yield) of 2,3,6-trimethyl-p-benzoquinone was included.

COMPARATIVE EXAMPLE 1

13.6 g (0.1 mole) of 2,3,6-trimethylphenol was dissolved in 100 g of acetic acid, and a mixture of 10 g of nitric acid and 20 g of water was added dropwise thereto at 20° – 30°C in 30 minutes, and the stirring was continued for another 30 minutes.

The same treatment as in Example 1 (A) was conducted to obtain 10.6 g (70.6 percent in yield) of 2,3,6-trimethyl-p-benzoquinone.

Additionally, this oxidation reaction occurred after an induction period, and the reaction started 10 minutes after the initiation of the dropwise addition.

COMPARATIVE EXAMPLE 2

13.6 g (0.1 mole) of 2,3,6-trimethylphenol was pulverized and dispersed in 40 g of water. Then, oxidation reaction was conducted in the same manner as in Example 4. The reaction proceeded so late that 2 hours were required at a room temperature. After conducting stream distillation, the same treatment as in Example 1 (B) was effected to obtain 4.28 g (28.6 percent in yield) of 2,3,6-trimethyl-p-benzoquinone.

COMPARATIVE EXAMPLE 3

17.0 g (0.1 mole) of 2,3,6-trimethyl-4-chlorophenol obtained in Example 1 (A) was dispersed in 40 g of water, and it was attempted to conduct oxidation by bubbling thereinto air under vigorous stirring at 60° – 80°C for 3 hours. However, oxidation reaction did not occur, and the starting material was recovered almost quantitatively.

While the invention has been described in detail and with reference to specific embodiments thereof, it will be apparent to one skilled in the art that various changes and modifications can be made therein without departing from the spirit and scope thereof.

What is claimed is:

1. A process for producing trimethyl-p-benzoquinone, which comprises oxidizing 2,3,5-or 2,3,6-trimethyl-p-halogenophenol, wherein the halogen moiety in said trimethyl-p-halogenophenol is chlorine, bromine or iodine, by contacting with nitric acid in the presence of a solvent selected from the group consisting of water, acetic acid, hexane, heptane, chloroform, dichloromethane, methyl chloride and carbon tetrachloride.

2. A process for producing trimethyl-p-benzoquinone as described in claim 1 wherein said trimethyl-p-halogenophenol is 2,3,6-trimethyl-p-halogenophenol.

3. A process for producing trimethyl-p-benzoquinone as described in claim 1, wherein said solvent is carbon tetrachloride.

4. A process for producing trimethyl-p-benzoquinone as described in claim 1, wherein said nitric acid is selected from the group consisting of dilute nitric acid, concentrated nitric acid and fuming nitric acid.

5. In an improved process for producing trimethyl-p-benzoquinone which comprises halogenating 2,3,5- or 2,3,6-trimethylphenol with a halogen selected from the group of chlorine, bromine and iodine at a temperature of from 0° to 100°C., in the absence of a catalyst or by contacting with a catalyst selected from the group consisting of iron powder, sodium acetate, aluminum chloride or iron chloride to obtain 2,3,5- or 2,3,6-trimethyl-4-halogenophenol and oxidizing the 2,3,5- or 2,3,6-trimethyl-4-halogenphenol, the improvement being said that said oxidizing is carried out by contacting said phenol with nitric acid in the presence of a solvent selected from the group consisting of water, acetic acid, hexane, heptane, chloroform, dichloromethane, methyl chloride and carbon tetrachloride.

6. A process for producing trimethyl-p-benzoquinone as described in claim 5 wherein both said halogenation reaction and said oxidation reaction are conducted in carbon tetrachloride as a solvent.

7. A process for producing trimethyl-p-benzoquinone as described in claim 5, wherein said catalyst is iodine when the halogen used in the halogenation is chlorine or bromine.

8. A process for producing trimethyl-p-benzoquinone as described in claim 5, wherein no catalyst is utilized in said halogenation.

9. A process for producing trimethyl-p-benzoquinone as described in claim 5, wherein acetic acid or carbon disulfide is used as a solvent for said halogenation.

10. A process for producing trimethyl-p-benzoquinone as described in claim 5, wherein said nitric acid is selected from the group consisting of dilute nitric acid, concentrated nitric acid and fuming nitric acid.

* * * * *